«12» United States Patent
Fackrell et al.

(10) Patent No.: US 8,618,268 B2
(45) Date of Patent: Dec. 31, 2013

(54) METHOD FOR SEPARATING FRACTIONS OF AVIAN EGGS EXCLUSIVELY CONTAINING IGA AND IGM ANTIBODIES

(76) Inventors: Hugh B. Fackrell, Windsor (CA); Linton W. Lee, Windsor (CA)

( * ) Notice: Subject to any disclaimer, the term of this patent is extended or adjusted under 35 U.S.C. 154(b) by 104 days.

(21) Appl. No.: 13/177,114

(22) Filed: Jul. 6, 2011

(65) Prior Publication Data
US 2013/0012688 A1   Jan. 10, 2013

(51) Int. Cl.
*A23J 1/00* (2006.01)
(52) U.S. Cl.
USPC ............ 530/412; 530/417; 530/418; 530/419
(58) Field of Classification Search
None
See application file for complete search history.

(56) References Cited

U.S. PATENT DOCUMENTS

2007/0238097 A1 * 10/2007 Fackrell .......................... 435/5

OTHER PUBLICATIONS

Beetham et al. "A comparison of three isolation methods for obtaining immunoglobulin A from turkey bile" Avian Diseaes 37: 1993, pp. 1026-1031.*
Dohms et al. "Metabolism and passive transfer of immunoglobulins in the turkey hen" Am J Vet Res, 39(9), pp. 1472-1481.*
Goudswaard et al. "The immunoglobulins of the Turkey (*Meleagris gallopavo*) isolation and characterization of IgG, IgM and IgA in body fluids, eggs and intraocular tissues" Poultry Science, 56, 1977, pp. 1847-1851.*
Rose et al. "Immunoglobulin classes in the hen's egg: their segregation in yolk and white" Eur. J. Immunol. 1974, 4, pp. 521-523.*

* cited by examiner

*Primary Examiner* — Daniel E Kolker
*Assistant Examiner* — James Rogers

(57) ABSTRACT

The present invention provides the method of obtaining IgA and IgM antibodies from chicken egg whites. The method involves separating chicken egg whites into two fractions which contain IgA and IgM antibodies exclusively. This separation method consists of raising the volume of the egg whites using purified water, lowering the pH of said volume, filtering the IgM fraction from said volume, precipitating the IgA fraction from the remaining volume, dialyzing the IgA fraction and drying the IgA and IgM fractions.

11 Claims, No Drawings

METHOD FOR SEPARATING FRACTIONS OF AVIAN EGGS EXCLUSIVELY CONTAINING IGA AND IGM ANTIBODIES

STATEMENT REGARDING FEDERALLY SPONSORED RESEARCH OR DEVELOPMENT

N/A

BACKGROUND OF THE INVENTION

Antibodies to various antigens have been a common diagnostic tool used by research labs in modern times. Any molecule, particle, hormone, bacteria, etc. of interest in research setting requires tracking. A simple method of tracking a particle of interest is the development antibodies to that particle. Antibodies may be labelled with enzymes and used in diagnostic tests, such as ELISA, to qualitatively or quantitatively track particles in a given sample.

Mammals are frequently the animals of choice for producing tracking antibodies as they are common, well known to those practiced in the art. While the amounts of antibody obtained from mammals are usually small they are usually sufficient for research purposes. Avian eggs, specifically from domestic chickens, have also been used to produce antibodies for research purposes. There are some advantages to using avian antibodies which include larger amounts and lower background cross-reactions with research samples. Avian antibodies used for research and other purposes are invariably egg yolk antibodies known as IgY.

The advantages and disadvantages of IgY over mammalian antibodies for research and tracking purposes is well known to those practiced in the art:

1. IgY as a single class of antibody is present in only the egg yolk while mammalian antibody classes are all mixed together in serum. The natural segregation of a single antibody class in the egg yolk makes isolation of the single antibody easy in comparison to processing serum to obtain a single mammalian antibody class.
2. Cross-reactions are a major complication in any antibody based diagnostic test. If Mammalian antibodies are used for research in mammalian systems, researchers run the risk of false positive results from activation of the complement system, activation of the clotting cascade and interference with rheumatoid factor. IgY antibodies do not have these cross-reactions in mammalian systems.
3. Chicken IgY antibodies may be freeze dried with little or no loss in functionality. Mammalian antibodies lose a great deal of their activity after freeze drying.
4. Production of egg antibodies from chicken eggs is inherently safe. Eggs are generally regarded as safe, and isolating IgY antibodies from egg yolk involved neither needles nor hazardous chemicals. Mammals must be bled on a regular basis using needles and exposure to blood products is virtually assured.

Avian IgA and IgM antibodies are known to be present only in the white portion of chicken eggs, just as IgY is known to be present only in the egg yolk. Multiple mentions of egg white IgA and IgM have been made in the literature, but only with regard to their existence as antibodies produced by the avian immune system or to the small amounts present in the white relative to the much more plentiful IgY in the yolk (Rose and Orlans, 1981). Since IgA and IgM in egg white are present in much smaller absolute amounts than IgY in the yolk, only IgY has been explored as a useful product on a commercial scale in either research and clinical diagnostics fields or health care fields.

A discussion of chicken immunology shows that immunization and subsequent boosting with a given immunogen gives rise to the multiple class of antibodies in eggs, IgM, IgA and IgY each specific to said immunogen (Kincade and Cooper, 1971; Martin and Leslie, 1974). Isotype switching shows that the portions of the antibodies, or binding sites, specific to a given immunogen are exactly the same in all classes of antibodies, IgM, IgA and IgY and are produced by the same B-lymphocytes.

The molecular structure of chicken antibodies have been studied and reviewed in Avian Immunology (2008, p. 109). IgM is characterized by a molecular weight of 823-954 kDa; the H chain has MW of ~70 kDa and the L chain has a MW of 22 kDa. IgA is characterized by a molecular size of 16.2 S.

IgA has been recognized as the first and best line of defense in avians, but commercial amounts of IgA are not readily available.

There is no publicly known procedure for commercial scale isolation of IgA and IgM antibodies from the egg whites of domestic chickens prior to this invention. Given the known advantages of using IgY from egg yolks, exploring the commercial scale advantages of IgA and IgM is desirable.

BRIEF SUMMARY OF THE INVENTION

Broadly, the present invention is directed to a method of isolating IgA and IgM antibodies from the egg white of a domestic chicken. The method comprising fractionating the white of said egg by raising the volume of the egg white using purified water, lowering the pH of said volume, filtering IgM fraction from said volume, salting out the IgA fraction from the remaining volume, dialyzing the IgA precipitate and drying the IgA and IgM fractions.

DETAILED DESCRIPTION OF THE INVENTION

The present invention relates to a new method of isolating IgA and IgM antibodies from the egg white of a domestic chicken. The laying hen transfers IgY, IgA and IgM antibodies to its egg. The commonly known IgY antibody in the egg yolk can be isolated from the egg yolk by a variety of methods known to those practiced in the art. IgA and IgM are only known to be isolated from the egg white, in large scale quantities, by the present invention.

Eggs are mechanically separated by use of a commercial or retail egg separator or other means. The egg whites containing the IgA and IgM may be pooled.

The total egg white volume is raised by four to five times its volume using purified water. The pH of the resulting volume is lowered to below 3.0 for best results. The egg whites are gently stirred using a glass rod or other similar means. Raising the volume using purified water serves to lower the ionic strength of the solution which allows only the more insoluble materials, such as IgM to precipitate. Lowering the pH of the egg whites allows them to be liquefied; without this step, precipitation of IgM and filtering is not effective.

The acid, purified water and egg white solution is refrigerated for eight to 24 hours to allow separation of IgM and IgA antibody fractions to occur.

The insoluble material which appears after separation has occurred is the IgM fraction of the egg white, while the aqueous solution contains the IgA fraction.

Filtering using coarse filters of between 15 and 30 microns is sufficient to separate the IgM in the insoluble material from the aqueous solution containing the IgA.

EXAMPLES

The following Examples are given for the purpose of illustration only and are not intended to limit the scope of the present invention.

Example 1

Ten eggs were collected on six consecutive days from two domestic chicken hens. The eggs were cracked and the yolks separated from the whites. Egg whites were pooled into a single volume totaling 225 ml.

Using water, purified by reverse osmosis, the total volume was raised to 900 ml. The pH of the egg white and water solution was lowered by the addition of 100 ml of 4% acetic acid. The resulting solution was stirred by hand using a glass rod then refrigerated for 18 hours.

After 18 hours, the lowered pH egg white and water solution had separated into an aqueous fraction and an insoluble fraction of mucous like material. The solution was filtered using coarse filters to remove the insoluble IgM fraction. The aqueous fraction was brought to ⅓ concentration of ammonium sulphate, the precipitate collected, dialyzed and lyophilized. Both fractions were further purified by ion exchange.

Both purified fractions were run through both native and reducing gel electrophoresis. Native gel electrophoresis of the soluble fraction of the egg white showed a band corresponding to a molecular size of 16.2 S indicating the presence of IgA. Native gel electrophoresis of the originally insoluble fraction showed a band in the 823-954 kDa range indicating the presence of IgM and not IgA. Reducing gel electrophoresis of the originally insoluble fraction showed bands at 70 kDa and 22 kDa indicating the presence of heavy and light chains of IgM antibodies.

Both purified fractions were tested independently by direct ELISA using goat antibodies to chicken IgA and goat antibodies to chicken IgM. Both ELISA tests showed the presence of IgA and IgM in their respective egg white fraction samples.

Native gel studies, reducing gel studies and direct ELISA studies demonstrate the presence of only IgA in the aqueous fraction and only IgM in the insoluble fraction after separation from egg whites.

REFERENCES

Davison, F., Kaspers, B, & Schat, K. A. (2008). Avian Immunology. Academic Press.

Kincade, P. W. and Cooper, M. D. (1971). Development and distribution of immunoglobulin-containing cells in the chicken. An immunofluorescent analysis using purified antibodies to mu, gamma and light chains. J. Immunol. 106, 371-382.

Martin, L. N. and Leslie, G. A. (1974) IgM-forming cells as the immediate precursor of IgA-producing cells during ontogeny of the immunoglobulin-producing system of the chicken. J. Immunol. 113, 120-126.

Rose, M. E. and Orlans, E. (1981). Immunoglobulins in the egg, embryo and young chick. Dev. Comp. Immunol. 5, 15-20.

We claim:

1. A method of obtaining avian IgA and IgM antibodies by fractionating the white of the egg of a domestic fowl hen by raising the volume of the egg white containing said antibodies using purified water, lowering the pH of said volume, filtering IgM fraction from said volume, precipitating the IgA fraction from the remaining volume, dialyzing the IgA fraction and drying the IgA and IgM fractions.

2. The method of claim 1, wherein said fowl is selected from the group consisting of a chicken, a duck, a goose, a turkey, a pheasant and a quail.

3. The method of claim 2, wherein said fowl is a chicken.

4. The method of claim 1, wherein purified water is used to raise the volume of the egg white by four to five times its volume.

5. The method of claim 1, wherein the pH of the volume is reduced to 3.0 or lower.

6. The method of claim 1, wherein the lowered pH solution is refrigerated for eight to 24 hours to allow separation to occur.

7. The method of claim 6, wherein the refrigerated solution is filtered using a coarse filter, to remove the insoluble IgM fraction of the egg white leaving the IgA in the remaining volume.

8. The method of claim 1, wherein the IgA volume is precipitated using ammonium sulphate.

9. The method of claim 1, wherein the salted IgA volume supernatant is removed, leaving the IgA precipitate.

10. The method of claim 1, wherein the IgA precipitate is dialyzed in purified water to remove ammonium sulphate.

11. The method of claim 1, wherein IgA and IgM fractions are dried.

* * * * *